US012399292B2

(12) United States Patent
Liu et al.

(10) Patent No.: US 12,399,292 B2
(45) Date of Patent: Aug. 26, 2025

(54) METHOD FOR DETERMINING CONNECTED AND NON-CONNECTED POROSITIES

(71) Applicant: ARAMCO SERVICES COMPANY, Houston, TX (US)

(72) Inventors: Chao Liu, Brookshire, TX (US); Dung T. Phan, Brookshire, TX (US); Younane N. Abousleiman, Norman, OK (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 514 days.

(21) Appl. No.: 17/814,380

(22) Filed: Jul. 22, 2022

(65) Prior Publication Data

US 2024/0027642 A1 Jan. 25, 2024

(51) Int. Cl.
*G01V 1/30* (2006.01)
*E21B 49/00* (2006.01)

(52) U.S. Cl.
CPC ............ *G01V 1/306* (2013.01); *E21B 49/006* (2013.01); *E21B 2200/20* (2020.05)

(58) Field of Classification Search
CPC ... G01V 1/306; E21B 49/006; E21B 2200/20; G01N 33/24
See application file for complete search history.

(56) References Cited

U.S. PATENT DOCUMENTS

2023/0383648 A1* 11/2023 Liu ..................... E21B 49/005

FOREIGN PATENT DOCUMENTS

CA  2904008 C * 10/2020 ............. E21B 49/00
CN  108562617 B  10/2020

OTHER PUBLICATIONS

Chao Liu et al., Poroelastodynamic responses of a dual-porosity dual-permeability material under harmonic loading, Jul. 1, 2021, Partial Differential Equations in Applied Mathematics, 4, pp. 1-6 (Year: 2021).*
Liu et al., Determination of the Connected and Isolated Porosities by a Poroelastodynamics Model, 2024, International Petroleum Technology Conference, IPTC-23741-EA, pp. 1-12 (Year: 2024).*

(Continued)

*Primary Examiner* — Mi'schita' Henson
(74) *Attorney, Agent, or Firm* — Osha Bergman Watanabe & Burton LLP

(57) ABSTRACT

Systems and methods for determining a connected porosity and a non-connected porosity in a fluid-saturated hydrocarbon reservoir are disclosed. The methods include obtaining at least one rock sample from the fluid-saturated hydrocarbon reservoir, determining, using a petrophysical sample analyzer, at least one petrophysical parameter of the rock sample, and measuring at least one of an elastic wave velocity and an elastic wave attenuation for each of a plurality of wave frequencies. The methods further include determining, using a computer processor, the connected porosity and the non-connected porosity of the rock sample using a dual-porosity single-permeability model based, at least in part, on at least one petrophysical parameter and at least one of the elastic wave velocity and the elastic wave attenuation.

17 Claims, 9 Drawing Sheets

(56) References Cited

OTHER PUBLICATIONS

M. Bai et al.; "Multiporosity/Multipermeability Approach to the Simulation of Naturally Fractured Reservoirs", Water Resources Research; vol. 29; No. 6; Jun. 1993; pp. 1621-1633 (13 pages).

Chao Liu; "Fundamental solutions to the transversely isotropic poroeslastodynamics Mandel's problem", International Journal for Numerical and Analytical Methods in Geomechanics; vol. 45; Issue 13; Jul. 24, 2021 (24 pages).

C. Liu and D. T. Phan; "Poroelastodynamic responses of a dual-porosity dual-permeability material under harmonic loading", Partial Differential Equations in Applied Mathematics; vol. 4; Dec. 2021 (6 pages).

Chao Liu; "Dual-Porosity Dual-Permeability Poroelastodynamics Analytical Solutions for Mandel's Problems", Journal of Applied Mechanics; vol. 88; Jan. 2021; pp. 1-10 (10 pages).

A. Mehrabian and C. Liu; "Mandel's problem reloaded", Journal of Sound and Vibration; vol. 492; Feb. 3, 2021 (16 pages).

S. R. Pride and J. G. Berryman; "Linear dynamics of double-porosity dual-permeability materials. I. Governing equations and acoustic attenuation", Physical Reviw E; vol. 68; No. 036603; Sep. 2003 (10 pages).

W. Yan et al.; "A robust NMR method to measure porosity of low porosity rocks", Microporous and Mesoporous Materials; vol. 269; Oct. 2018 (5 pages).

\* cited by examiner

METHOD FOR DETERMINING CONNECTED AND NON-CONNECTED POROSITIES

BACKGROUND

The knowledge of connected and non-connected porosities plays an essential role in the estimation of in-situ hydrocarbon reserves of a reservoir and the determination of favorable target production regions. There are some common methods, such as mercury intrusion porosimetry and nuclear magnetic resonance (NMR), for the determination of the porosity of a rock. Some of them allow to determine the total porosity, i.e., the summation of connected and non-connected porosity, e.g., computed tomography (CT) and scanning electron microscopy (SEM). Others can detect the connected porosity only, e.g., mercury intrusion porosimetry and gas expansion porosimetry. To determine the non-connected porosity, two kinds of measurements can be applied in the same kind of rock samples, e.g., CT to determine the total porosity and mercury intrusion porosimetry to determine the connected porosity. The non-connected porosity can be obtained by subtracting the connected porosity from the total porosity. However, there exist no method for simultaneously determining connected and non-connected porosity.

Poroelastodynamic theory allows for modeling of elastic waves propagation in fluid saturated rocks with both connected and non-connected porosity. Wave phenomena, including dispersion and attenuation, occur simultaneously due to the coupled motions of the rock matrix and fluids in pore spaces. These wave effects can be analytically predicted, given as input a set of physical parameters including connected and non-connected porosities. This suggests a possible application of the theory for estimating both porosity values.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments related to methods for determining a connected porosity and a non-connected porosity in a fluid-saturated hydrocarbon reservoir are disclosed. The methods include obtaining at least one rock sample from the fluid-saturated hydrocarbon reservoir, determining, using a petrophysical sample analyzer, at least one petrophysical parameter of the rock sample, and measuring at least one of an elastic wave velocity and an elastic wave attenuation for each of a plurality of wave frequencies. The methods further include determining, using a computer processor, the connected porosity and the non-connected porosity of the rock sample using a dual-porosity single-permeability model based, at least in part, on at least one petrophysical parameter and at least one of the elastic wave velocity and the elastic wave attenuation.

In general, in one aspect, embodiments related to a non-transitory computer readable medium storing instructions executable by a computer processor with functionality for determining a connected porosity and a non-connected porosity in a fluid-saturated hydrocarbon reservoir are disclosed. The instructions include functionality for determining, using a petrophysical sample analyzer at least one petrophysical parameter of a fluid-saturated rock sample, and measuring at least one of an elastic wave velocity and an elastic wave attenuation for each of a plurality of wave frequencies. The instructions further include functionality for determining, using a computer processor, a connected porosity and a non-connected porosity of the rock sample using a dual-porosity single-permeability model based, at least in part, on at least one petrophysical parameter and the at least one of the elastic wave velocity and the elastic wave attenuation.

In general, in one aspect, embodiments related to a system configured for determining a connected porosity and a non-connected porosity in a fluid-saturated hydrocarbon reservoir are disclosed. The system includes a petrophysical sample analyzer, used to measure at least one petrophysical parameter of a fluid-saturated rock sample, and an ultrasonic measurement cell, to measure at least one of an elastic wave velocity and an elastic wave attenuation of the fluid-saturated rock sample. The system further includes a computer memory device configured to receive at least one petrophysical parameter of the fluid-saturated rock sample, and receive at least one of an elastic wave velocity and an elastic wave attenuation for each of a plurality of wave frequencies. The computer system is further configured to determine a connected porosity and a non-connected porosity of the rock sample using a dual-porosity single-permeability model based, at least in part, on at least one petrophysical parameter and the at least one of the elastic wave velocities and the elastic wave attenuation.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
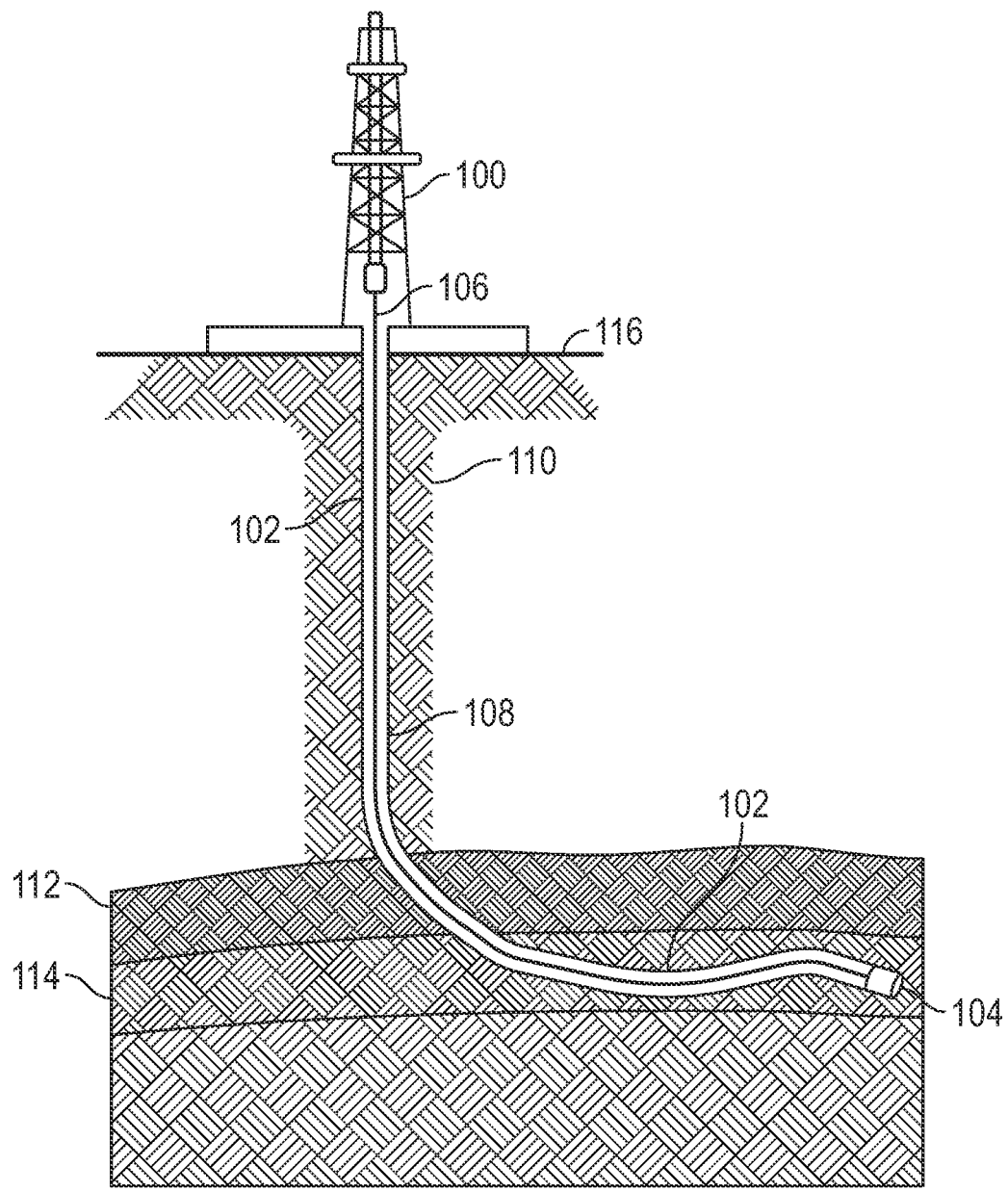
FIG. 1 shows a drilling system in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-8, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to a rock sample includes reference to one or more such rock samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

Obtaining measurements of the connected and non-connected porosity in a reservoir allows for accurate estimates of the total quantity of recoverable hydrocarbons in the reservoir. It also permits modeling the fluid flow through the reservoir and determining the optimal placement of production wells as part of a hydrocarbon reservoir development plan. Current methods do not allow for the simultaneous measurement of both connected and non-connected porosities; some methods estimate total porosity, others predict connected porosity. A method is disclosed herein that is able to predict both connected and non-connected porosity from reservoir rock samples by measuring the velocity and attenuation of elastic waves through the samples and comparing the measurements to those predicted by a new poroelastodynamic theory. The velocities and attenuation measurements are obtained over a range of harmonic frequencies in an experimental apparatus.

FIG. 1 illustrates systems in accordance with one or more embodiments. Specifically, FIG. 1 illustrates a well (102) that may be drilled by a drill bit (104) attached by a drillstring (106) to a drill rig (100) located on the surface of the earth (116). A curved wellbore path (108) may traverse a plurality of overburden layers (110) and one or more cap-rock layers (112) to a hydrocarbon reservoir (114). Rock samples from the hydrocarbon reservoir (114) or other layers may be collected for analysis from cores collected while drilling or extracted from the wall of the well (102), usually by a wireline tool. Cores may be extracted by percussion or mechanical drilling and may have orientations parallel or perpendicular to the direction of the wellbore path (108). The rock samples may be used to estimate the connected and non-connected porosity of the subsurface layers.

Figure 2:
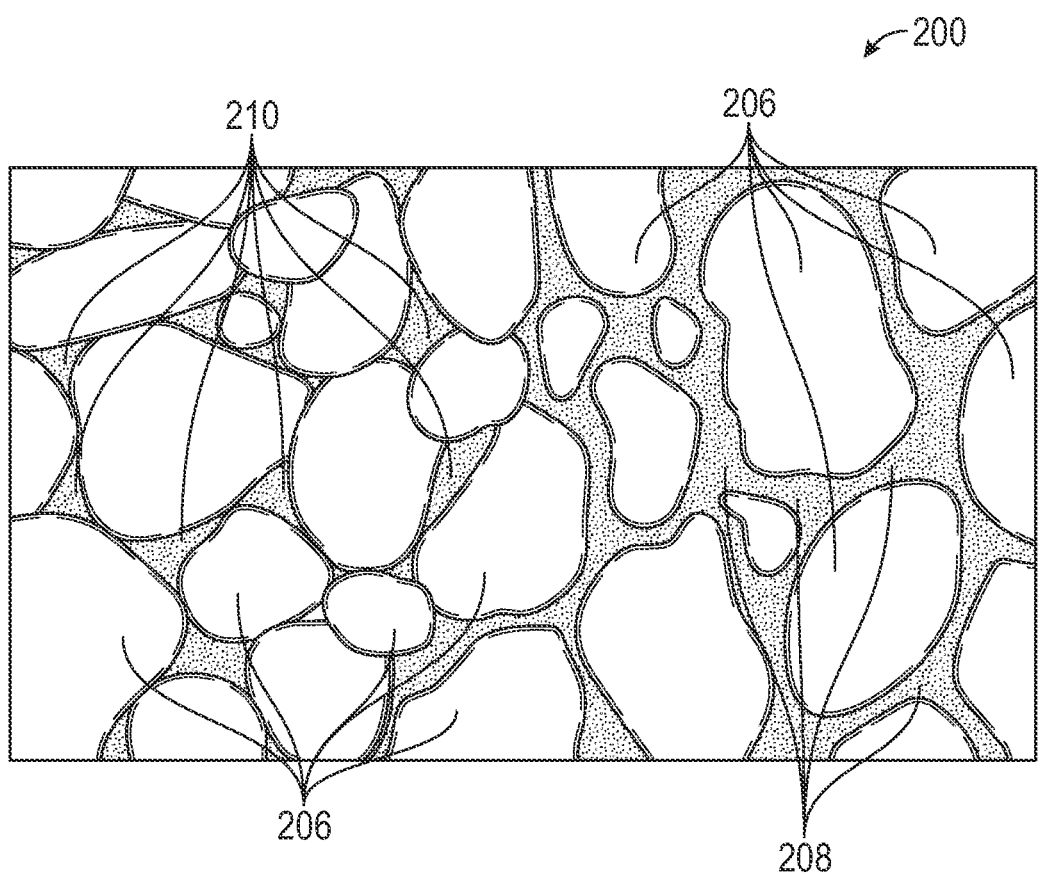
FIG. 2 shows connected and non-connected porosity.

FIG. 2 depicts a rock sample in accordance with one or more embodiments. Specifically, it depicts a rock sample (200) with the rock grains (206) that make up the sample. Between the rock grains (206) are spaces or voids that are typically termed pores (208, 210). Pores connected to their neighboring pores by channels between the rock grains (206) may be called connected pores (208). When subjected to a pressure gradient, fluid may flow between connected pores (208) making the rock sample (200) permeable. Pores non-connected to their neighbors may be called non-connected pores (210). Fluid present in non-connected pores (210) may not flow through the rock sample (200) and will not contribute to the permeability of the rock sample (200). Porosity measures the cumulative volume of all the pores (208, 210) as a fraction of the rock sample (200) volume and is typically presented as a percentage, such as 20%. Porosity may be divided into connected porosity and non-connected porosity. The connected porosity measures the cumulative volume of the connected pores (208) as a fraction of the rock sample (200) volume and non-connected porosity measures the cumulative volume of the non-connected pores (210) as a fraction of the rock sample (200) volume. The laws of physics encapsulated in mathematical equations permit the modeling of elastic wave propagation through a porous medium. Different simplifying physical assumptions lead to different equations. Dual-porosity dual-permeability theory allows for modeling a heterogeneous medium containing two types of material, each with different petrophysical properties. The governing equations for the dual-porosity dual-permeability poroelastodynamics are presented and discussed in "*Linear dynamics of double-porosity dual-permeability materials. I. Governing equations and acoustic attenuation*" Pride, S. R. and Berryman, J. G., Physical Review E 68, no. 3 (2003): 036603. Under the plane strain condition, the constitutive equations are expressed as $$\sigma_{xx} = (\lambda + 2G)\frac{\partial u_x}{\partial x} + \lambda\frac{\partial u_z}{\partial z} - \bar{\alpha}_1 p_1 - \bar{\alpha}_2 p_2 \tag{1}$$

-continued $$\sigma_{yy} = \lambda \frac{\partial u_x}{\partial x} + \lambda \frac{\partial u_z}{\partial z} - \overline{\alpha}_1 p_1 - \overline{\alpha}_2 p_2 \quad (2)$$

$$\sigma_{zz} = \lambda \frac{\partial u_x}{\partial x} + (\lambda + 2G)\frac{\partial u_z}{\partial z} - \overline{\alpha}_1 p_1 - \overline{\alpha}_2 p_2 \quad (3)$$

$$\sigma_{xz} = G\left(\frac{\partial u_x}{\partial z} + \frac{\partial u_z}{\partial x}\right) \quad (4)$$

$$\zeta_1 = \overline{\alpha}_1 \left(\frac{\partial u_x}{\partial x} + \frac{\partial u_z}{\partial z}\right) + \frac{p_1}{M_{11}} + \frac{p_2}{M_{12}} \quad (5)$$

$$\zeta_2 = \overline{\alpha}_2 \left(\frac{\partial u_x}{\partial x} + \frac{\partial u_z}{\partial z}\right) + \frac{p_1}{M_{12}} + \frac{p_2}{M_{22}} \quad (6)$$

where $\sigma_{ij}$ is the stress component, $u_i$ is the displacement component in the i-direction, $\lambda$ and G are the average Lamé parameters of the dual-porosity rock, $\overline{\alpha}_1$ and $\overline{\alpha}_2$ are the effective Biot's coefficients, $\zeta_1$ and $\zeta_2$ are fluid content variations, $M_{ij}$ are the effective Biot's moduli. Neglecting body forces and considering the accelerations of solid grains and pore fluids in the dual-porosity system, the equilibrium equation takes the form $$\nabla \cdot \sigma = \rho \ddot{u} + \rho_f \dot{w}_1 + \rho_f \dot{w}_2 \quad (7)$$

where $\sigma$ is the stress tensor, $\rho$ is the bulk density, $\rho_f$ is the fluid density, u is the displacement vector of solid, $w_i = v_i \phi_i (U_i - u)$ is the specific displacement vector of fluid in porous medium i, $\phi_i$ is the porosity of porous medium i. Neglecting cross-coupling terms in the permeability tensor, Darcy's law with inertial effects for a dual-porosity dual-permeability porous medium is expressed as $$\dot{w}_1 = -\frac{k_1}{\mu}\left(\nabla p_1 + \rho_f \ddot{u} + \frac{\tau_1 \rho_f}{v_1 \phi_1}\dot{w}_1 + \frac{\rho_{23}}{v_1 v_2 \phi_1 \phi_2}\dot{w}_2\right) \quad (8)$$

$$\dot{w}_2 = -\frac{k_2}{\mu}\left(\nabla p_2 + \rho_f \ddot{u} + \frac{\rho_{23}}{v_1 v_2 \phi_1 \phi_2}\dot{w}_1 + \frac{\tau_2 \rho_f}{v_2 \phi_2}\dot{w}_2\right) \quad (9)$$

where $k_1$ and $k_2$ are the permeabilities, $\mu$ is the fluid viscosity, $\tau_1$ and $\tau_2$ are the tortuosities of pore spaces, $\rho_{23}$ is defined by $$\rho_{23} = \frac{\rho_f}{2}[(\tau - 1)\phi - (\tau_1 - 1)v_1\phi_1 - (\tau_2 - 1)/v_2\phi_2],$$

where $\phi$ is the average porosity defined by $\phi = v_1 \phi_1 + v_2 \phi_2$, and $\tau$ is the average tortuosity that is defined by $$\tau = \frac{\phi[v_2 \phi_1 + (3 - v_2)]}{(3 - 2v_2)\phi_1 + 2v_2 \tau_1}.$$

Accounting for the inter-porosity fluid exchange between pore fluids in the dual-porosity dual-permeability porous medium, the equations of mass conservation are written as $$\dot{\zeta}_1 = -\nabla \cdot \dot{w}_1 + \gamma(p_2 - p_1) \quad (10)$$

$$\dot{\zeta}_2 = -\nabla \cdot \dot{w}_2 + \gamma(p_2 - p_1) \quad (11)$$

where the dot stands for the derivative with respect to time, $\gamma$ is the inter-porosity fluid exchange coefficient.

Based on the theory of dual-porosity dual-permeability poroelastodynamics disclosed in the previous section, the theory of dual-porosity single-permeability poroelastodynamics is used to simulate a fluid-saturated rock with both connected and non-connected pore spaces. The connected and non-connected porosities are denoted by porosity 1 and porosity 2, respectively. We set $\zeta_2 = 0$, $k_2 = 0$, $w_2 = 0$, and $\gamma = 0$. As a result, the governing equations for the dual-porosity single-permeability porous medium are expressed as $$\sigma_{xx} = (\lambda + 2G)\frac{\partial u_x}{\partial x} + \lambda \frac{\partial u_z}{\partial z} - \overline{\alpha}_1 p_1 - \overline{\alpha}_2 p_2 \quad (12)$$

$$\sigma_{yy} = \lambda \frac{\partial u_x}{\partial x} + \lambda \frac{\partial u_z}{\partial z} - \overline{\alpha}_1 p_1 - \overline{\alpha}_2 p_2 \quad (13)$$

$$\sigma_{zz} = \lambda \frac{\partial u_x}{\partial x} + (\lambda + 2G)\frac{\partial u_z}{\partial z} - \overline{\alpha}_1 p_1 - \overline{\alpha}_2 p_2 \quad (14)$$

$$\sigma_{xz} = G\left(\frac{\partial u_x}{\partial z} + \frac{\partial u_z}{\partial x}\right) \quad (15)$$

$$\zeta_1 = \overline{\alpha}_1 \left(\frac{\partial u_x}{\partial x} + \frac{\partial u_z}{\partial z}\right) + \frac{p_1}{M_{11}} + \frac{p_2}{M_{12}} \quad (16)$$

$$0 = \overline{\alpha}_2 \left(\frac{\partial u_x}{\partial x} + \frac{\partial u_z}{\partial z}\right) + \frac{p_1}{M_{12}} + \frac{p_2}{M_{22}} \quad (17)$$

$$\nabla \cdot \sigma = \rho + \rho \ddot{u} + \rho_f \dot{w}_1 \quad (18)$$

$$\dot{w}_1 = -\frac{k_1}{\mu}\left(\nabla p_1 + \rho_f \ddot{u} + \frac{\tau_1 \rho_f}{v_1 \phi_1}\dot{w}_1\right) \quad (19)$$

$$\dot{\zeta}_1 = -\nabla \cdot \dot{w}_1 \quad (20)$$

Assuming that all variables are of $e^{-i\omega t}$ time dependence, a combination of equations (16, 17, 20) gives $$p_1 = a_{11} \nabla \cdot u + a_{12} \nabla \cdot w_1 \quad (21)$$

$$p_2 = a_{21} \nabla \cdot u + a_{22} \nabla \cdot w_1 \quad (22)$$

where $$a_{11} = \frac{\overline{\alpha}_1 M_{11} M_{12}^2 - \overline{\alpha}_2 M_{11} M_{12} M_{22}}{M_{11} M_{22} - M_{12}^2} \quad (23)$$

$$a_{12} = \frac{M_{11} M_{12}^2}{M_{11} M_{22} - M_{12}^2} \quad (24)$$

$$a_{21} = \frac{-\overline{\alpha}_1 M_{11} M_{12} M_{22} + \overline{\alpha}_2 M_{12}^2 M_{22}}{M_{11} M_{22} - M_{12}^2} \quad (25)$$

$$a_{22} = -\frac{M_{11} M_{12} M_{22}}{M_{11} M_{22} - M_{12}^2} \quad (26)$$

Substitution of constitutive equations (12-15, 21, 22) into equation (18) gives $$(\lambda + G - \overline{\alpha}_1 a_{11} - \overline{\alpha}_2 a_{21})\nabla(\nabla \cdot u) + G\nabla^2 u - (\overline{\alpha}_1 a_{12} + \overline{\alpha}_2 a_{22})\nabla(\nabla \cdot w_1) + \omega^2 \rho u + \omega^2 \rho_f w_1 = 0 \quad (27)$$

Substitution of equations (21, 22) into equation (19) leads to $$a_{11}\nabla(\nabla \cdot u) + a_{12}\nabla(\nabla \cdot w_1) = \omega^2 \rho_f u + \left(\omega^2 \frac{\tau_1 \rho_f}{v_1 \phi_1} + \frac{i\omega}{\kappa_{11}}\right) w_1 \quad (28)$$

Equations (27, 28) provide a closed set of equations for the determination of u and $w_1$.

To determination wave velocities we begin with the displacement vectors, expressed in the following forms $$u = u_s + u_p; \quad w_1 = w_{1s} + w_{1p} \quad (29)$$

where the following conditions are satisfied $$\nabla \cdot u_s = \nabla \cdot w_{1s} = \nabla \times u_p = \nabla \times w_{1p} = 0 \quad (30)$$

Applying the curl operator, i.e., $\nabla \times$, to equations (27, 28) gives $$v_s^2 \nabla^2 u_s + \omega^2 u_s = 0 \quad (31)$$

$$w_{1s} = b_{11} u_S \quad (32)$$

where $$v_s = \sqrt{\frac{G}{\rho - \frac{\rho_f^2}{b_{11}}}} \quad (33)$$

$$b_{11} = \frac{\tau_1 \rho_f}{v_1 \phi_1} + \frac{i}{\omega \kappa_{11}} \quad (34)$$

Substituting equation (29) into equations (27, 28), applying the divergence operator, i.e., $\nabla \cdot$, and considering that $\nabla(\nabla \cdot X_p) = \nabla^2 X_p$ holds for any curl-free field $X_p$, we have $$\begin{bmatrix} n_{11}\nabla^2 + \omega^2 \rho & n_{12}\nabla^2 + \omega^2 \rho_f \\ a_{11}\nabla^2 - \omega^2 \rho_f & a_{12}\nabla^2 - \omega^2 b_{11} \end{bmatrix} \cdot \begin{bmatrix} u_p \\ w_{1p} \end{bmatrix} = \begin{bmatrix} 0 \\ 0 \end{bmatrix} \quad (35)$$

where $$n_{11} = \lambda + 2G - \bar{\alpha}_1 a_{11} - \bar{\alpha}_2 a_{21}; \quad n_{12} = -(\bar{\alpha}_1 a_{12} + \bar{\alpha}_2 a_{22}) \quad (36)$$

Equation (35) can be factorized as follows $$A_4 \nabla^4 + A_2 \nabla^2 + A_0 = 0 \quad (37)$$

where $$A_4 = a_{12} n_{11} - a_{11} n_{12};$$

$$A_2 = \omega^2 (a_{12}\rho - b_{11}n_{11} + n_{12}\rho_f - a_{11}\rho_f)$$

$$A_0 = \omega^4 (\rho_f^2 - \rho b_{11}) \quad (38)$$

The two roots of equation (37) are expressed as $$X_1 = \frac{-A_2 + \sqrt{A_2^2 - 4A_0 A_4}}{2A_4}; \quad X_2 = \frac{-A_2 - \sqrt{A_2^2 - 4A_0 A_4}}{2A_4} \quad (39)$$

Therefore, the two compressional wave velocities take the form $$v_{p1} = \sqrt{\frac{\omega^2}{-X_1}}; \quad v_{p2} = \sqrt{\frac{\omega^2}{-X_2}} \quad (40)$$

Wave attenuation is calculated based on the definition of the following inverse of quality factor $$Q^{-1} = 2 \left| \frac{v_i}{v_r} \right| \quad (41)$$

where $v_i$ and $v_r$ are the imaginary and real parts of the velocities $v_s$, $v_{p1}$, and $v_{p2}$.

Petrophysical parameters (e.g., Young's modulus, Poisson ratio, Skempton's coefficient, Biot's coefficient, permeability, tortuosity) are present in the dual-porosity single permeability equations. The values of these petrophysical parameters may be based on rock samples (200) taken from a hydrocarbon reservoir (114) and may be measured in a petrophysical sample analyzer or determined from well log data. Fixing the values of these parameters in the dual-porosity single-permeability theory, the relationship of phase velocity versus frequency may be determined for shear waves and compressional waves for varying values of connected and non-connected porosity. Similarly, given fixed values of the petrophysical parameters, the relationship of attenuation versus frequency may also be determined for both compressional waves and shear waves for varying values of connected and non-connected porosity.

Figure 3:
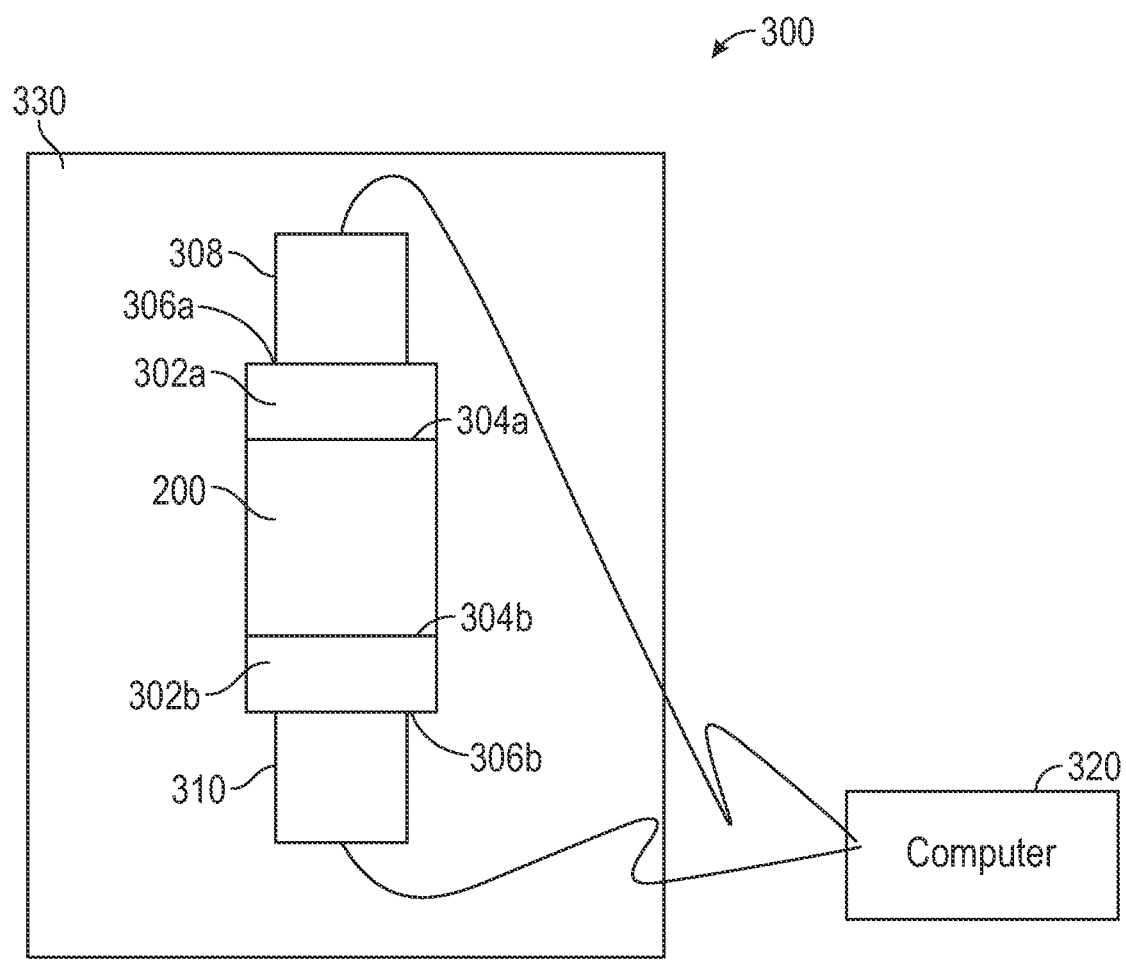
FIG. 3 shows a sonic measurement apparatus for transmitting and recording seismic signals through rock samples in accordance with one or more embodiments.

FIG. 3 depicts a system in accordance with one or more embodiments. Specifically, FIG. 3 shows a sonic measurement apparatus (300) that measures the velocities and attenuations of elastic waves in a rock sample (200). The sonic measurement apparatus (300) comprises a sonic signal generator (308), a sonic signal receiver (310), and a computer (320). In some embodiments the rock sample (200) may be a cylindrical rock sample. The rock sample (200) may be confined by an inner surface (304a) of a first impermeable rigid plate (302a) at a first end of the rock sample (200) and by an inner surface (304b) of a second impermeable rigid plate (302b) at a second (opposing) end of the rock sample (200). The outer surface (306a) of the first impermeable rigid plate (302a) may be in contact with a sonic signal generator (308). The outer surface (306b) of the second impermeable rigid plate (302b) may be in contact to a sonic signal receiver (310). The sonic signal generator (308) may be connected to a computer (320) such that electrical signals, e.g., firing instructions, may be communicated between the computer (320) and the sonic signal generator (308). The computer may be one similar to that shown and described with respect to FIG. 8 below. Similarly, the sonic signal receiver (310) may be connected to a computer (320) such that electrical signals, e.g., detected sonic signals, may be communicated between the sonic signal receiver (310) and the computer (320). The rock sample (200), the two impermeable rigid plates (302a, 302b), the sonic signal generators (308) and the sonic signal receiver (310) may be contained within a fluid-filled enclosure (330).

The sonic signal generator (308), controlled by the computer (320), vibrates the first impermeable rigid plate (302a) at specified harmonic frequencies. This, in turn, vibrates the inner surface of the first impermeable rigid plate (304a) causing sonic waves to travel through the rock sample (200). These transmitted sonic signals then vibrate the inner surface of the second impermeable rigid plate (304b) causing the second impermeable rigid plate (302b) to also vibrate. The sonic signals are recorded by the sonic signal receiver (310) attached to the second impermeable rigid plate (302b). The sonic signal receiver (310) transmits the sonic signals to a computer (320) where they are recorded.

Figure 4A:
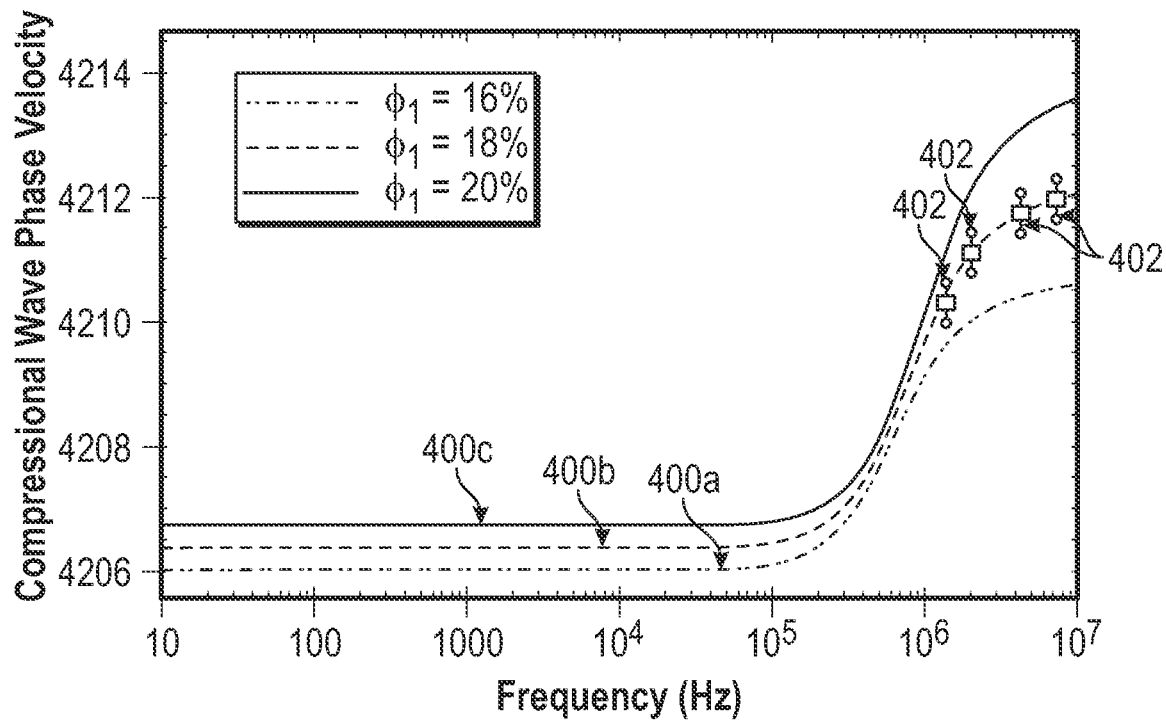
FIG. 4A shows the relationship between frequency and phase velocity of compressional waves for a range of connected porosity values.

FIG. 4A shows curves (400a, 400b, 400c) of compressional wave phase velocity versus frequency for three different values of connected porosity (208). The curves were calculated using the dual-porosity single-permeability theory presented above. Specifically, curve (400a) corresponds to 16% connected porosity (208), curve (400b) corresponds to 18% connected porosity (208), and curve (400c) corresponds to 20% connected porosity (208). Data points (402) represent actual laboratory measurements from the sonic measurement apparatus (300).

Figure 4B:
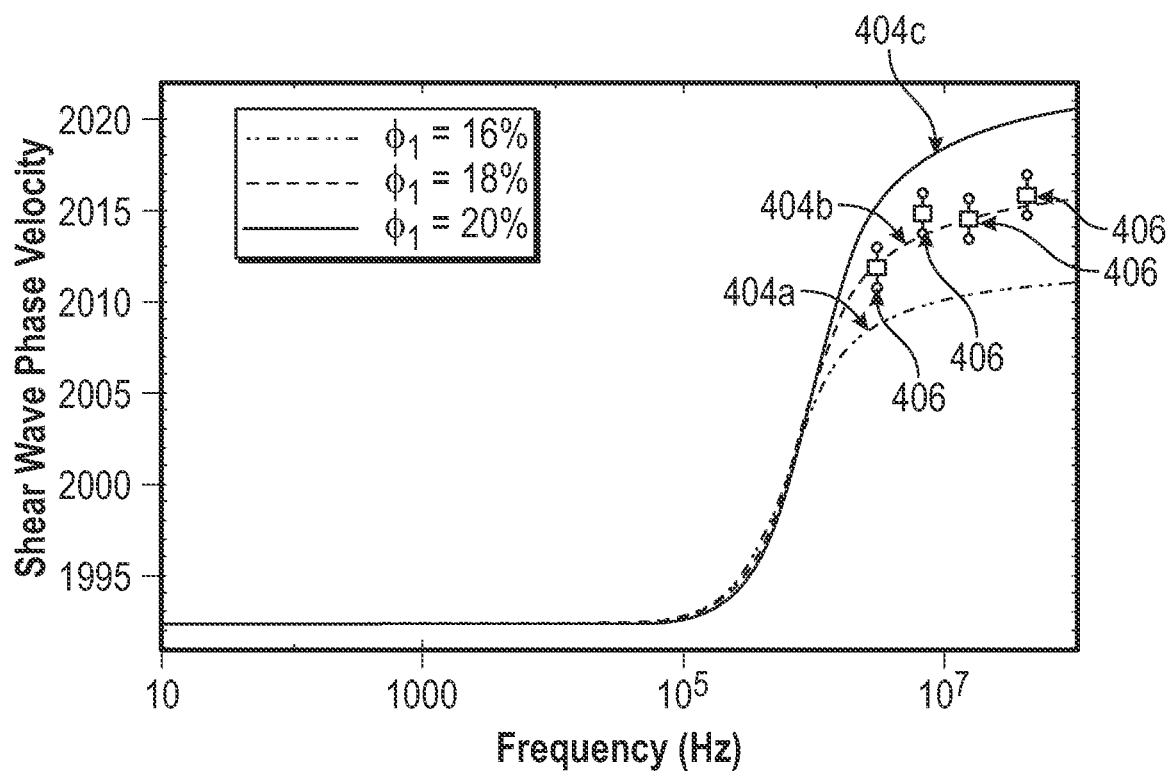
FIG. 4B shows the relationship between frequency and phase velocity of shear waves for a range of connected porosity values.

FIG. 4B shows curves (404a, 404b, 404c) of shear wave phase velocity versus frequency for three different values of connected porosity (208) (16%, 18%, and 20%). The curves were calculated using the dual-porosity single-permeability theory presented above. Specifically, curve (404a) corresponds to 16% connected porosity (208), curve (404*b*) corresponds to 18% connected porosity (208), and curve (404*c*) corresponds to 20% connected porosity (208). Data points (406) represent actual laboratory measurements from the sonic measurement apparatus (300).

Figure 5A:
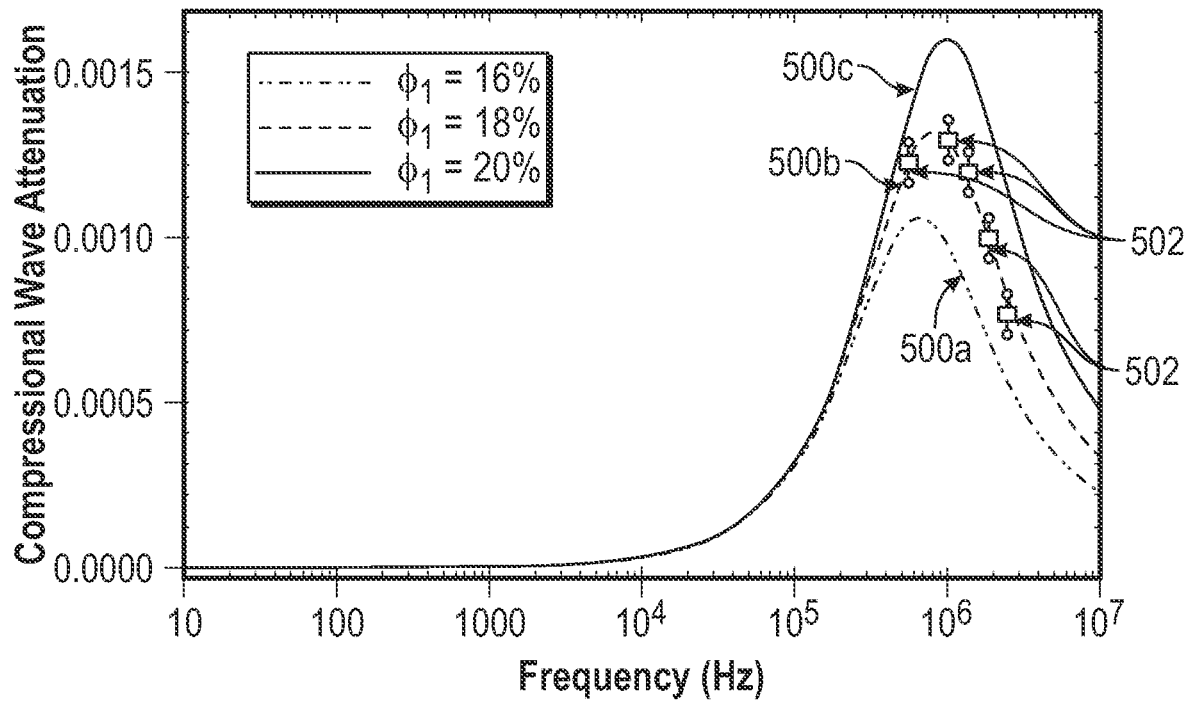
FIG. 5A shows the relationship between frequency and attenuation of compressional waves for a range of connected porosity values.
Figure 5B:
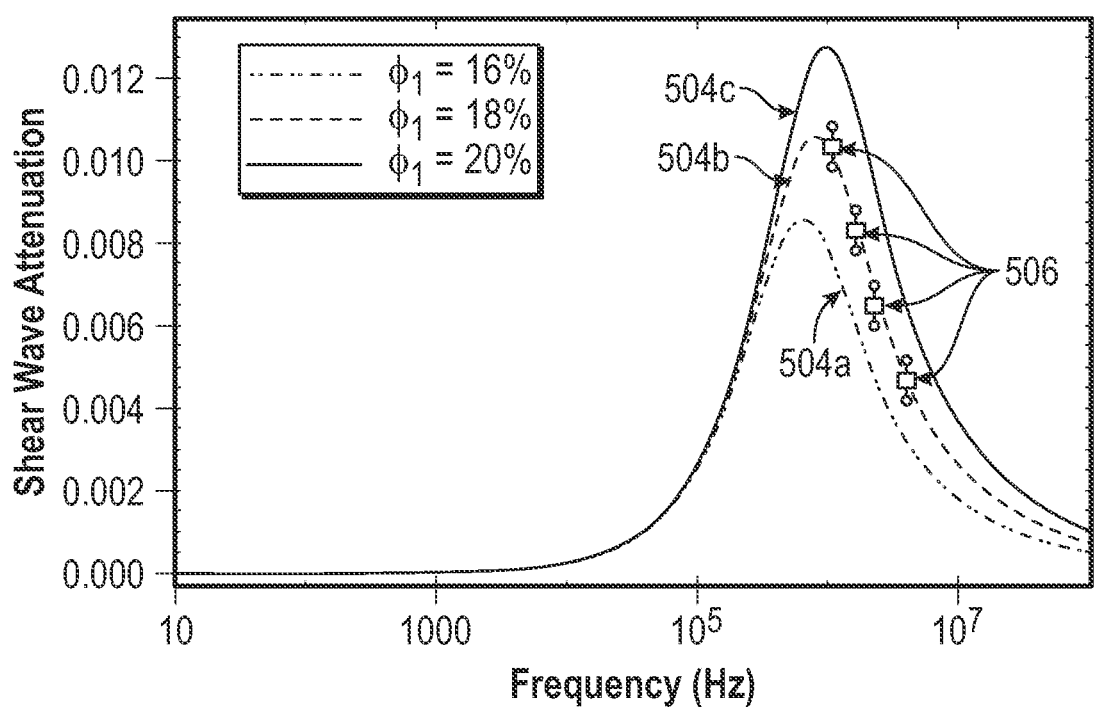
FIG. 5B shows the relationship between frequency and attenuation of shear waves for a range of connected porosity values.

FIG. 5A shows curves (500*a*, 500*b*, 500*c*) of compressional wave attenuation versus frequency for three different values of connected porosity (208) (16%, 18%, and 20%). FIG. 5B shows curves (504*a*, 504*b*, 504*c*) of shear wave attenuation versus frequency for three different values of connected porosity (208) (16%, 18%, and 20%). The curves in FIGS. 5A and 5B were calculated using dual-porosity single-permeability theory. Specifically, curves (500*a*) and (504*a*) corresponds to 16% connected porosity (208), curve (500*b*) and (504*b*) corresponds to 18% connected porosity (208), and curve (500*c*) and (504*c*) corresponds to 20% connected porosity (208). The relationship between compressional wave attenuation and frequency corresponds to a first compressional wave traveling through the porous medium, as predicted by dual-porosity single-permeability theory. Data points (502) and (506) represent actual laboratory measurements from the sonic measurement apparatus (300).

Figure 6:
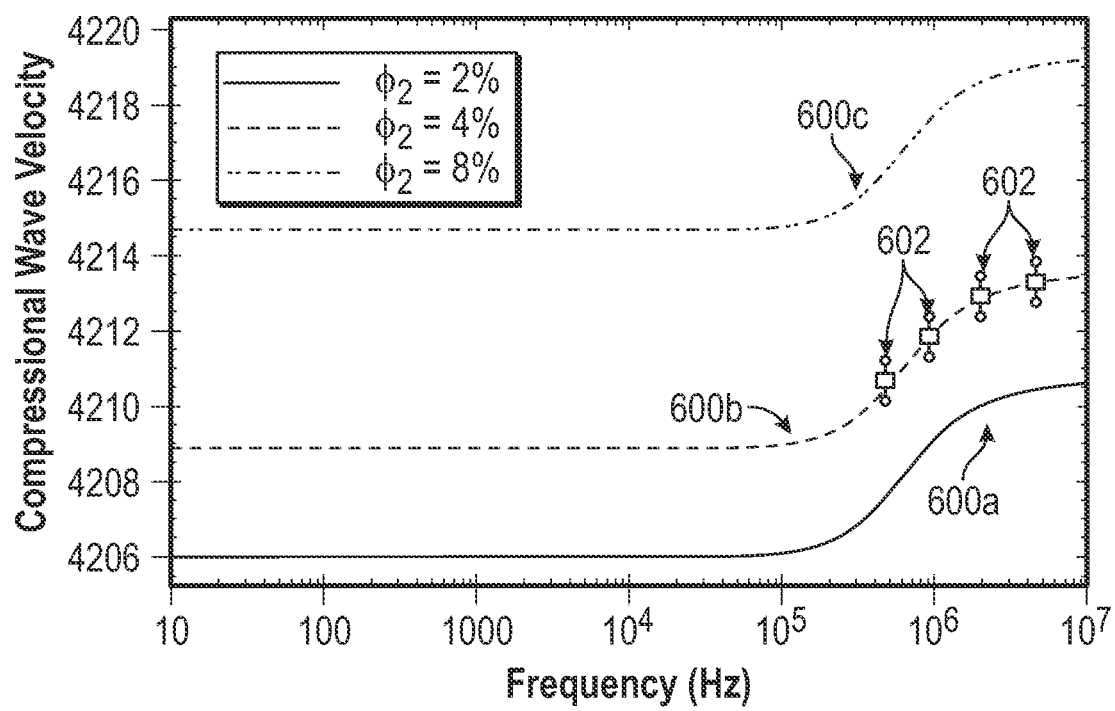
FIG. 6 shows the relationship between frequency and phase velocity of compressional waves for a range of non-connected porosity values.

FIG. 6 shows curves (600*a*, 600*b*, 600*c*) of compressional wave phase velocity versus frequency for three different values of non-connected porosity (210) (2%, 4%, and 8%). Specifically, curve (600*a*) corresponds to 2% non-connected porosity (210), curve (600*b*) corresponds to 4% non-connected porosity (210), and curve (600*c*) corresponds to 8% non-connected porosity (210). These curves were calculated using dual-porosity single-permeability theory. In this case, increasing the non-connected porosity value increases compressional wave phase velocity across all frequencies. This relationship between compressional wave velocity and frequency corresponds to a second compressional wave traveling through the porous medium, as predicted by dual-porosity single-permeability theory. Data points (602) represent actual laboratory measurements from the sonic measurement apparatus (300).

A data assimilation technique searches over all possible combinations of values of connected and non-connected porosity to find curves for compressional wave phase velocity (FIGS. 4A and 6), shear wave phase velocity (FIG. 4B), compressional wave attenuation (FIG. 5A), and shear wave attenuation (FIG. 5B) that best fit the measured data points. The data assimilation technique may include regression or a grid search over the possible connected and non-connected porosity values to find the value that minimizes a least-squares misfit between the curves and the observed data points, but other data-fitting methods and misfit metrics known to a person of ordinary skill in the art may be used without departing from the scope of the invention.

Figure 7:
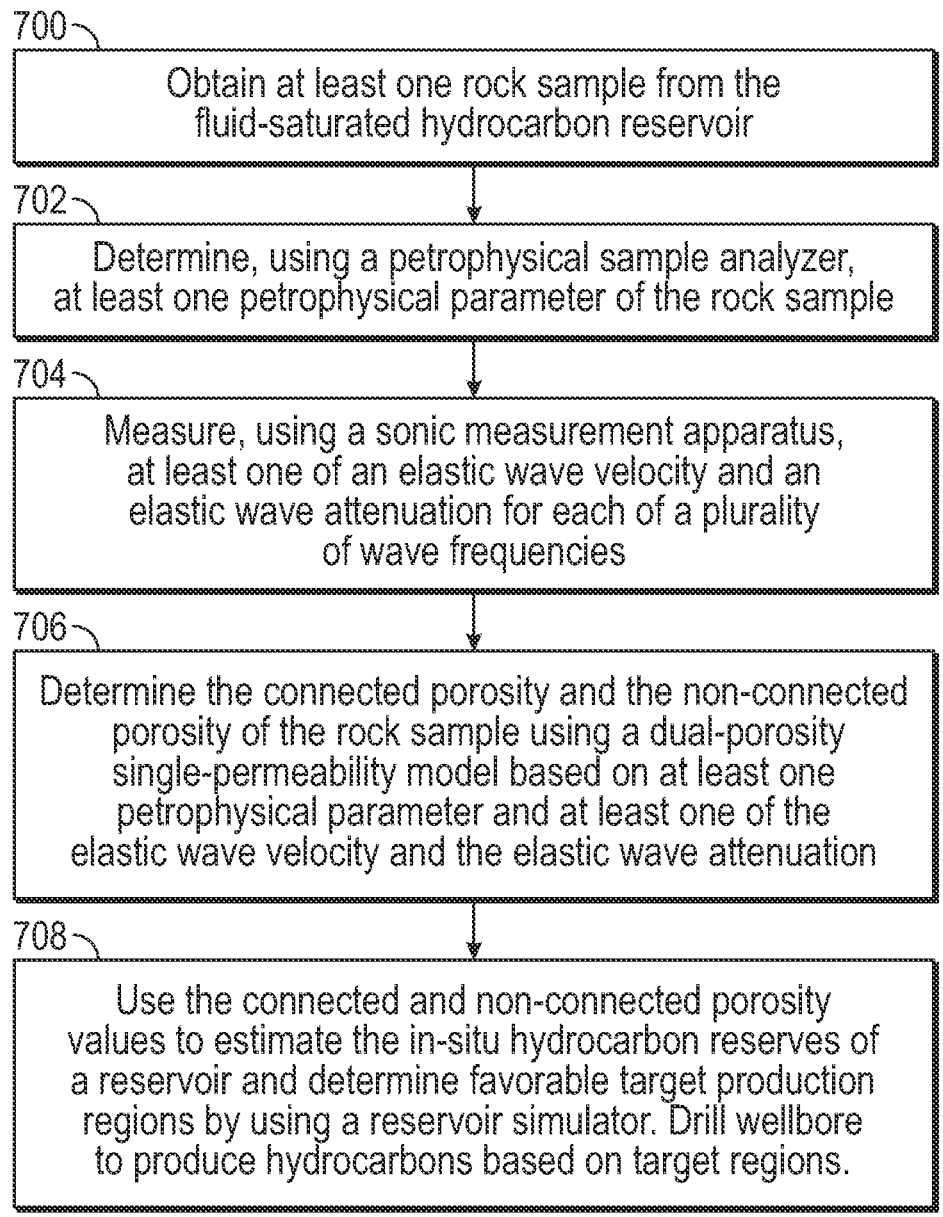
FIG. 7 shows a flowchart for measuring connected and non-connected porosity.

In accordance with one or more embodiments, FIG. 7 shows a flowchart for the method disclosed herein. In the first step (700), rock samples may be obtained from cores drilled in a hydrocarbon reservoir (114) or other layers in the subsurface during a well drilling operation. In step 702, petrophysical parameters (e.g., Young's modulus, Poisson ratio, Skempton's coefficient, Biot's coefficient, permeability, tortuosity) may be measured using a petrophysical sample analyzer or obtained from well log data.

In accordance with one or more embodiments, in step 704 the rock sample (200) may be placed into the sonic measurement apparatus (300) where the sonic characteristic of the sample may be measured. That is, the sonic measurement apparatus is used to measure at least one of an elastic wave velocity and an elastic wave attenuation for each of a plurality of wave frequencies. Pure harmonic compressional waves and shear waves may be transmitted through the rock sample (200) and recorded on a computer (310). For each of a number of frequencies, compressional wave velocity values and shear wave velocity values may be determined from a propagation time of the waves and the spatial distance between the two impermeable rigid plates (304*a*) and (304*b*). Attenuation values (for both compressional and shear waves) may be inferred from the recorded data using any manual or automated method known to the average practitioner of the art.

In step 706, the inferred data points are compared to the values predicted by the dual-porosity single-permeability poroelastic theory. First, for the fixed values of the petrophysical parameters, the value of connected porosity may be varied, each time determining the dependence upon frequency of a first compressional wave phase velocity (Equation 40), a shear wave phase velocity (Equation 33), a compressional wave attenuation for the first compressional wave (Equation 41), and a shear wave attenuation (Equation 41). Further, for the fixed values of the petrophysical parameters, the value of non-connected porosity may be varied, each time determining the dependence upon frequency of a second compressional wave phase velocity for the second compressional wave (Equation 40). A data assimilation technique may be used to compare the measured and predicted data points to determine which values of connected and non-connected porosity best reproduce the observed compressional wave phase velocities, shear wave phase velocity, compressional wave attenuation, and shear wave attenuation as a function of harmonic signal frequency. The best-fitting values of connected and non-connected porosity may be determined to be the values of the connected and non-connected porosity of the sample. The best-fitting values of connected and non-connected porosity are used in step 708 to estimate the in-situ hydrocarbon reserves of a reservoir and determine favorable target production regions by using a reservoir simulator. A wellbore may be drilled to produce hydrocarbons based on target production regions.

Figure 8:
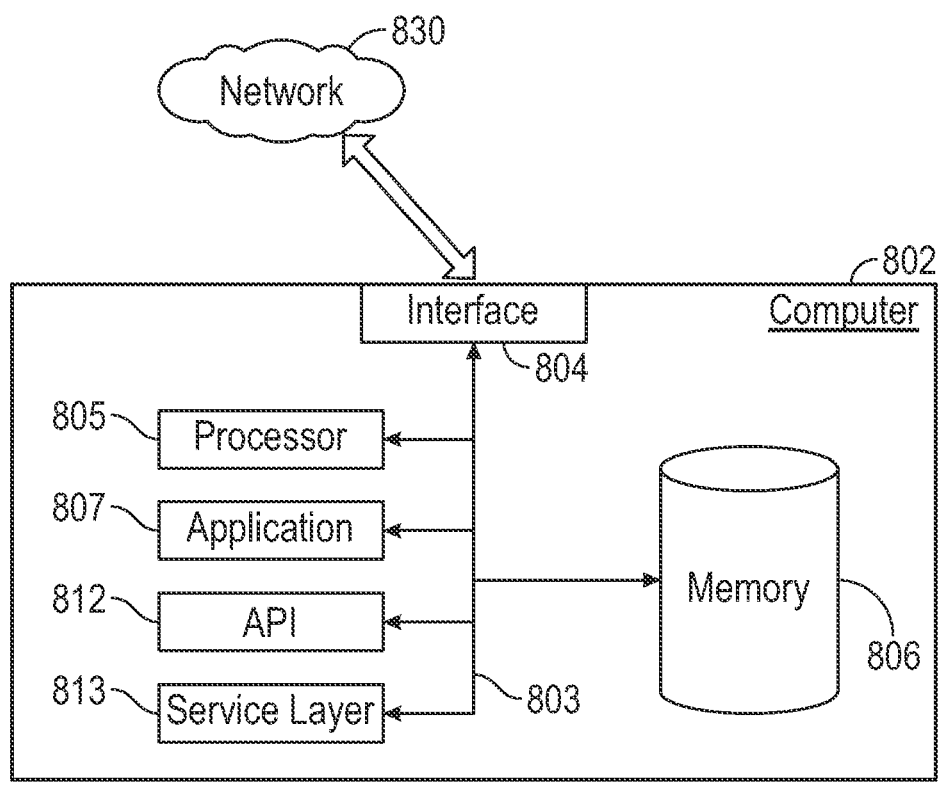
FIG. 8 shows a computer system in accordance with one or more embodiments.

FIG. 8 depicts a block diagram of a computer system (802) used to provide computational functionalities associated with described algorithms, methods, functions, processes, flows, and procedures as described in this disclosure, according to one or more embodiments. The illustrated computer (802) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (802) may include an input device, such as a keypad, keyboard, touch screen, or other device that can accept user information, and an output device that conveys information associated with the operation of the computer (802), including digital data, visual, or audio information (or a combination of information), or a GUI.

The computer (802) can serve in a role as a client, network component, a server, a database or other persistency, or any other component (or a combination of roles) of a computer system for performing the subject matter described in the instant disclosure. The illustrated computer (802) is communicably coupled with a network (830). In some implementations, one or more components of the computer (802) may be configured to operate within environments, including cloud-computing-based, local, global, or other environment (or a combination of environments).

At a high level, the computer (802) is an electronic computing device operable to receive, transmit, process, store, or manage data and information associated with the described subject matter. According to some implementations, the computer (802) may also include or be communicably coupled with an application server, e-mail server, web server, caching server, streaming data server, business intelligence (BI) server, or other server (or a combination of servers).

The computer (802) can receive requests over network (830) from a client application (for example, executing on another computer (802)) and responding to the received requests by processing the said requests in an appropriate software application. In addition, requests may also be sent to the computer (802) from internal users (for example, from a command console or by other appropriate access method), external or third-parties, other automated applications, as well as any other appropriate entities, individuals, systems, or computers.

Each of the components of the computer (802) can communicate using a system bus (803). In some implementations, any or all of the components of the computer (802), both hardware or software (or a combination of hardware and software), may interface with each other or the interface (804) (or a combination of both) over the system bus (803) using an application programming interface (API) (812) or a service layer (813) (or a combination of the API (812) and service layer (813)). The API (812) may include specifications for routines, data structures, and object classes. The API (812) may be either computer-language independent or dependent and refer to a complete interface, a single function, or even a set of APIs. The service layer (813) provides software services to the computer (802) or other components (whether or not illustrated) that are communicably coupled to the computer (802). The functionality of the computer (802) may be accessible for all service consumers using this service layer. Software services, such as those provided by the service layer (813), provide reusable, defined business functionalities through a defined interface. For example, the interface may be software written in JAVA, C++, or other suitable language providing data in extensible markup language (XML) format or another suitable format. While illustrated as an integrated component of the computer (802), alternative implementations may illustrate the API (812) or the service layer (813) as stand-alone components in relation to other components of the computer (802) or other components (whether or not illustrated) that are communicably coupled to the computer (802). Moreover, any or all parts of the API (812) or the service layer (813) may be implemented as child or sub-modules of another software module, enterprise application, or hardware module without departing from the scope of this disclosure.

The computer (802) includes an interface (804). Although illustrated as a single interface (804) in FIG. 2, two or more interfaces (804) may be used according to particular needs, desires, or particular implementations of the computer (802). The interface (804) is used by the computer (802) for communicating with other systems in a distributed environment that are connected to the network (830). Generally, the interface (804) includes logic encoded in software or hardware (or a combination of software and hardware) and operable to communicate with the network (830). More specifically, the interface (804) may include software supporting one or more communication protocols associated with communications such that the network (830) or interface's hardware is operable to communicate physical signals within and outside of the illustrated computer (802).

The computer (802) includes at least one computer processor (805). Although illustrated as a single computer processor (805) in FIG. 2, two or more processors may be used according to particular needs, desires, or particular implementations of the computer (802). Generally, the computer processor (805) executes instructions and manipulates data to perform the operations of the computer (802) and any algorithms, methods, functions, processes, flows, and procedures as described in the instant disclosure.

The computer (802) also includes a memory (806) that holds data for the computer (802) or other components (or a combination of both) that can be connected to the network (830). For example, memory (806) can be a database storing data consistent with this disclosure. Although illustrated as a single memory (806) in FIG. 2, two or more memories may be used according to particular needs, desires, or particular implementations of the computer (802) and the described functionality. While memory (806) is illustrated as an integral component of the computer (802), in alternative implementations, memory (806) can be external to the computer (802).

The application (807) is an algorithmic software engine providing functionality according to particular needs, desires, or particular implementations of the computer (802), particularly with respect to functionality described in this disclosure. For example, application (807) can serve as one or more components, modules, applications, etc. Further, although illustrated as a single application (807), the application (807) may be implemented as multiple applications (807) on the computer (802). In addition, although illustrated as integral to the computer (802), in alternative implementations, the application (807) can be external to the computer (802).

There may be any number of computers (802) associated with, or external to, a computer system containing computer (802), wherein each computer (802) communicates over network (830). Further, the term "client," "user," and other appropriate terminology may be used interchangeably as appropriate without departing from the scope of this disclosure. Moreover, this disclosure contemplates that many users may use one computer (802), or that one user may use multiple computers (802).

In some embodiments, a reservoir simulator comprises functionality for simulating the flow of fluids, including hydrocarbon fluids such as oil and gas, through a hydrocarbon reservoir (114) composed of porous, permeable reservoir rocks in response to natural and anthropogenic pressure gradients. The reservoir simulator may be used to predict changes in fluid flow, including fluid flow into a well (102) penetrating the reservoir (114) as a result of planned well drilling, as well as fluid injection and extraction. For example, the reservoir simulator may be used to predict changes in hydrocarbon production rate that would result from the injection of water into the reservoir (114) from wells around the reservoirs periphery.

The reservoir simulator may use a reservoir model that contains a digital description of the physical properties of the rocks as a function of position within the reservoir and the fluids within the pores of the porous, permeable reservoir rocks at a given time. In some embodiments, the digital description may be in the form of a dense 3D grid with the physical properties of the rocks and fluids defined at each node. In some embodiments, the 3D grid may be a cartesian grid, while in other embodiments the grid may be an irregular grid.

The physical properties of the rocks and fluids within the reservoir (114) may be obtained from a variety of geological and geophysical sources. For example, remote sensing geophysical surveys, such as seismic surveys, gravity surveys, and active and passive source resistivity surveys, may be employed. In addition, data collected, such as well logs and core data acquired in wells (102) penetrating the reservoir may be used to determine physical and petrophysical properties along the segment of the well trajectory (102) traversing the reservoir (114).

Figure 9:
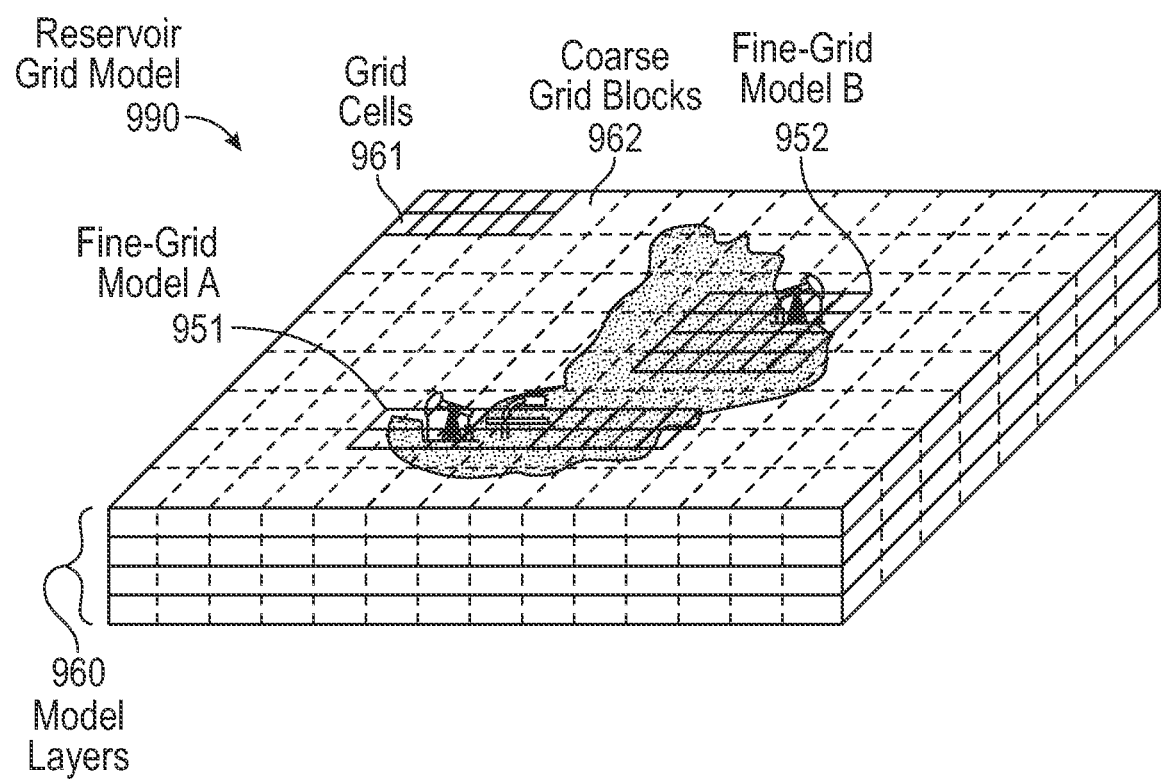
FIG. 9 shows a reservoir simulator in accordance with one or more embodiments.

FIG. 9 shows a schematic diagram in accordance with one or more embodiments. FIG. 9 shows a reservoir grid model (990) that corresponds to the hydrocarbon reservoir (114). More specifically, the reservoir grid model (990) includes grid cells (961) that may refer to an original cell of a reservoir grid model as well as coarse grid blocks (962) that may refer to an amalgamation of original cells of the reservoir grid model. For example, a grid cell may be the case of a 1×1 block, where coarse grid blocks may be of sizes 2×2, 4×4, 8×8, etc. Both the grid cells (961) and the coarse grid blocks (962) may correspond to columns for multiple model layers (960) within the reservoir grid model (990).

Prior to performing a reservoir simulation, local grid refinement and coarsening may be used to increase or decrease grid resolution in a certain area of reservoir grid model. For example, various reservoir properties, e.g., permeability, porosity or saturations, may correspond to a discrete value that is associated with a particular grid cell or coarse grid block (962). However, by using discrete values to represent a portion of a geological region, a discretization error may occur in a reservoir simulation. Thus, finer grids may reduce discretization errors as the numerical approximation of a finer grid is closer to the exact solution, however, at a higher computational cost. As shown in FIG. 9, for example, the reservoir grid model (990) may include various fine-grid models (i.e., fine-grid model A (951), fine-grid model B (952)), that are surrounded by coarse block regions. Likewise, the original reservoir grid model without any coarsening may also be a fine-grid model. In some embodiments, a reservoir grid model (or multiple reservoir grid models) may be used to preform reservoir simulations.

Reservoir simulators solve a set of mathematical governing equations that represent the physical laws that govern fluid flow in porous, permeable media. For example, the flow of a single-phase slightly compressible oil with a constant viscosity and compressibility the equations capture Darcy's law, the continuity condition and the equation of state and may be written as:

$$\nabla^2 p(x, t) = \frac{\varphi \mu c_t}{k} \frac{\partial p(x, t)}{\partial t} \quad \text{Equation (42)}$$

where p represents fluid in the reservoir, x is a vector representing spatial position and t represents time. $\varphi$, $\mu$, $c_t$, and k represent the physical and petrophysical properties of porosity, fluid viscosity, total combined rock and fluid compressibility, and permeability, respectively. $\nabla^2$ represents the spatial Laplacian operator.

More complicated equations are required when more than one fluid, or more than one phase, e.g., liquid and gas, are present in the reservoir. In a more complex model, the values of connected and non-connected porosity may also enter the mathematical equations that model fluid flow through the reservoir.

For a digital reservoir model, the governing equations must be solved by one of a variety of numerical methods, such as, without limitation, explicit or implicit finite-difference methods, explicit or implicit finite element methods, or discrete Galerkin methods.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A method for determining a connected porosity and a non-connected porosity in a fluid-saturated hydrocarbon reservoir, comprising:

obtaining at least one rock sample from the fluid-saturated hydrocarbon reservoir;

determining, using a petrophysical sample analyzer, at least one petrophysical parameter of the rock sample;

measuring at least one of an elastic wave velocity and an elastic wave attenuation for each of a plurality of wave frequencies;

determining, using a computer processor, the connected porosity and the non-connected porosity of the rock sample using a dual-porosity single-permeability model based, at least in part, on at least one petrophysical parameter and at least one of the elastic wave velocity and the elastic wave attenuation determining a hydrocarbon reservoir development plan for the hydrocarbon reservoir using a reservoir simulator based, at least in part, on the connected porosity and on the non-connected porosity; and drilling a wellbore to produce hydrocarbons from the hydrocarbon reservoir based, at least in part, on the hydrocarbon reservoir development plan.

2. The method of claim 1, wherein measuring the elastic wave velocity comprises:

exciting elastic waves on a first surface of the rock sample;

detecting elastic waves on a second surface of the rock sample;

determining a propagation time of the elastic waves from the first surface to the second surface; and determining the velocity of the elastic waves based on the propagation time and a spatial distance between the first surface and the second surface.

3. The method of claim 1, wherein determining the connected porosity and the non-connected porosity, further comprises minimizing a metric of misfit between the measured and predicted elastic wave velocities and the measured and predicted elastic wave attenuations, wherein the predicted elastic wave velocities and predicted elastic wave attenuations are calculated using the dual-porosity single-permeability model.

4. The method of claim 3, wherein the metric of misfit comprises a least-squares misfit function.

5. The method of claim 1, wherein the elastic waves are compressional elastic waves.

6. The method of claim 1, wherein at least one petrophysical parameter is selected from the group consisting of a Young's modulus, a bulk modulus, Poisson's ratio, a Skempton's coefficient, a Biot's coefficient, a permeability, and a tortuosity.

7. A non-transitory computer readable medium storing instructions executable by a computer processor, the instructions comprising functionality for:
determining, using a petrophysical sample analyzer at least one petrophysical parameter of a fluid-saturated rock sample;
measuring at least one of an elastic wave velocity and an elastic wave attenuation for each of a plurality of wave frequencies; and
determining, using a computer processor, a connected porosity and a non-connected porosity of the rock sample using a dual-porosity single-permeability model based, at least in part, on at least one petrophysical parameter and the at least one of the elastic wave velocity and the elastic wave attenuation
wherein measuring the elastic wave velocity comprises;
exciting elastic waves on a first surface of the rock sample,
detecting elastic waves on a second surface of the rock sample,
determining a propagation time of the elastic waves from the first surface to the second surface, and
determining the velocity of the elastic waves based on the propagation time and a spatial distance between the first surface and the second surface.

8. The non-transitory computer readable medium of claim 7, wherein determining the connected porosity and the non-connected porosity, further comprises minimizing a metric of misfit between the measured and predicted elastic wave velocities and the measured and predicted elastic wave attenuations, wherein the predicted elastic wave velocities and predicted elastic wave attenuations are calculated using the dual-porosity single-permeability model.

9. The non-transitory computer readable medium of claim 8, wherein the metric of misfit comprises a least-squares misfit function.

10. The non-transitory computer readable medium of claim 7, wherein the elastic wave is a compressional elastic wave.

11. The non-transitory computer readable medium of claim 7, wherein at least one petrophysical parameter is selected from the group consisting of a Young's modulus, a bulk modulus, Poisson's ratio, a Skempton's coefficient, a Biot's coefficient, a permeability, and a tortuosity.

12. A system, comprising:
a petrophysical sample analyzer, to measure at least one petrophysical parameter of a fluid-saturated rock sample;
an ultrasonic measurement cell, to measure at least one of an elastic wave velocity and an elastic wave attenuation of the fluid-saturated rock sample;
a computer memory device configured to:
receive at least one petrophysical parameter of the fluid-saturated rock sample;
receive at least one of an elastic wave velocity and an elastic wave attenuation for each of a plurality of wave frequencies; and
determine a connected porosity and a non-connected porosity of the rock sample using a dual-porosity single-permeability model based, at least in part, on at least one petrophysical parameter and the at least one of the elastic wave velocities and the elastic wave attenuation
a reservoir simulator for determining a hydrocarbon reservoir development plan based, at least in part, on the connected porosity and on the non-connected porosity; and
a drilling system to drill a wellbore to produce hydrocarbons from the hydrocarbon reservoir based, at least in part, on the hydrocarbon reservoir development plan.

13. The system of claim 12, wherein measuring the elastic wave velocity comprises:
exciting the elastic wave on a first surface of the rock sample;
detecting the elastic wave on a second surface of the rock sample;
determining a propagation time of the elastic wave from the first surface to the second surface; and
determining the elastic wave velocity based on the propagation time and a spatial distance between the first surface and the second surface.

14. The system of claim 12, wherein determining the connected porosity and the non-connected porosity further comprises minimizing a metric of misfit between the measured and predicted elastic wave velocities and the measured and predicted elastic wave attenuations, wherein the predicted elastic wave velocities and predicted elastic wave attenuations are calculated using the dual-porosity single-permeability model.

15. The system of claim 14, wherein the metric of misfit comprises a least-squares misfit function.

16. The system of claim 12, wherein the elastic wave is a compressional elastic wave.

17. The system of claim 12, wherein at least one petrophysical parameter is selected from the group consisting of a Young's modulus, a bulk modulus, Poisson's ratio, a Skempton's coefficient, a Biot's coefficient, a permeability, and a tortuosity.

* * * * *